(12) United States Patent
Peschel et al.

(10) Patent No.: US 7,547,378 B2
(45) Date of Patent: Jun. 16, 2009

(54) METHOD FOR THE PURIFICATION OF DIMETHYLACETAMIDE (DMAC)

(75) Inventors: Werner Peschel, Freinsheim (DE);
Hartmut Schoenmakers, Dossenheim (DE); Klaus Althaus, Mannheim (DE);
Tanja Kirchner, Nierstein (DE);
Hartmut Staatz, Heidelberg (DE)

(73) Assignee: BASF Aktiengesellschaft (DE)

( * ) Notice: Subject to any disclaimer, the term of this patent is extended or adjusted under 35 U.S.C. 154(b) by 666 days.

(21) Appl. No.: 10/551,360

(22) PCT Filed: Apr. 5, 2004

(86) PCT No.: PCT/EP2004/003595
§ 371 (c)(1),
(2), (4) Date: Sep. 28, 2005

(87) PCT Pub. No.: WO2004/087639
PCT Pub. Date: Oct. 14, 2004

(65) Prior Publication Data
US 2006/0219545 A1 Oct. 5, 2006

(30) Foreign Application Priority Data
Apr. 3, 2003 (DE) ................. 103 15 214

(51) Int. Cl.
*B01D 3/42* (2006.01)
*C07C 231/24* (2006.01)

(52) U.S. Cl. ............... 203/2; 203/99; 203/DIG. 19; 564/216

(58) Field of Classification Search ............ 203/1–2, 203/17, 99, DIG. 19; 564/142, 216
See application file for complete search history.

(56) References Cited

U.S. PATENT DOCUMENTS

| | | | |
|---|---|---|---|
| 3,300,531 A | 1/1967 | James et al. | |
| 3,557,207 A | 1/1971 | Hammond et al. | |
| 3,687,820 A | 8/1972 | Akell et al. | |
| 6,946,060 B2 * | 9/2005 | Gentilcore | .......... 203/2 |

FOREIGN PATENT DOCUMENTS

| | | |
|---|---|---|
| FR | 1406279 | 6/1965 |
| WO | WO-2004/002926 | 1/2004 |

* cited by examiner

*Primary Examiner*—Virginia Manoharan
(74) *Attorney, Agent, or Firm*—Connolly Bove Lodge & Hutz

(57) ABSTRACT

The invention relates to a process for distillatively purifying crude dimethylacetamide (crude DMAc) comprising DMAc, low boilers and high boilers 5 by removing the low boilers and the high boilers to obtain pure DMAc in one of the column configurations listed hereinbelow:
(I) a main column (MC) with sidestream column (SC) or
(II) a dividing wall column (DWC),
which operating at least the main column (MC) in column configuration (I) and the dividing wall column (DWC) in column configuration (II) at a top pressure in the range from 0.5 to 1.8 bar absolute.

18 Claims, 2 Drawing Sheets

METHOD FOR THE PURIFICATION OF DIMETHYLACETAMIDE (DMAC)

RELATED APPLICATIONS

Figure 1:
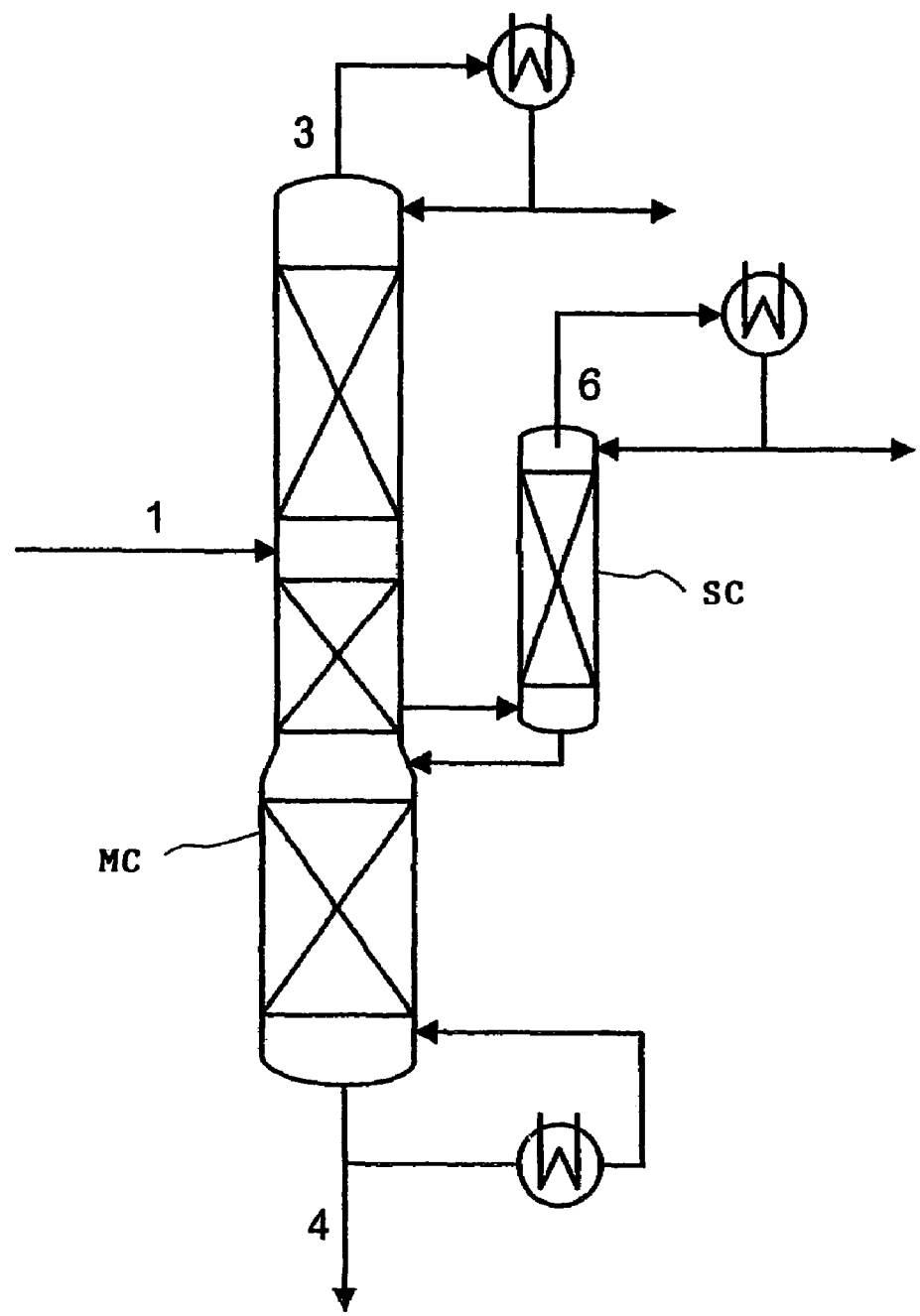

This application is a national stage application (under 35 U.S.C. 371) of PCT/EP2004/003595 filed Apr. 5, 2004 which claims benefit to German application 103 15 214.8 filed Apr. 3, 2003.

The invention relates to a process for distillatively purifying crude dimethylacetamide. Dimethylacetamide is abbreviated to DMAc hereinbelow.

DMAc is used predominantly as a solvent, for example as a solvent for solution spinning of elastic polyurethane block copolymers which are known by the brand names Spandex® or Lycra®, as well as or the production of hollow fibers.

In order to be able to obtain high quality fibers in solution spinning, the DMAc used is required to fulfill the following specifications: water content <100 ppm, pH between 6.5 and 7, and specific electrical conductivity <0.6 µS/cm, or of less than 0,2 µS/cm. The electric conductivity of pure DMAc is basically caused by its content of impurities, like acids mainly acetic acid and salts, especially the anerine salts of acetic acid. The given specifications of pure DMAc with respect to gH-value and electric conductivity correspond to a content of acetic acid of less than 50 weight-ppm.

DMAc which fulfills these specification requirements is referred to hereinbelow as pure DMAc.

In contrast, crude DMAc refers to a mixture comprising DMAc which does not fulfill the above-defined specification requirements.

Existing plants for distillative purification of DMAc are operated under reduced pressure, in order to effectively suppress decomposition reactions of DMAc and thus to ensure the achievement of the specification requirements.

However, it has been found that the specification requirements frequently cannot be fulfilled in distillation plants which have been operated under reduced pressure as hitherto customary.

Document FR-PS 1,406,279 describes a process for producing DMAc by reaction of acetic acid with dimethyl amine and destination separation of the reaction mixture in a two-column-arrangement, the first column being operated at atmospheric pressure or slightly above atmospheric pressure, a bottom temperature between 165 and 170° C., a temperature at the top between 95 and 105° C. and a temperature in the region of the column feed, which is located at about the middle of the column, of between 100 and 200° C. A top stream containing dimethyl amine and water on a gaseous or liquid bottom stream, containing DMAc acetic acid and monomethyl acetamide are drawn off from the first column. This bottom stream is fed to about the middle region of a second column and separated therein into a top stream containing purified DMAc and a bottom stream, containing the terneary azeotrope of acitic acid, DMAc and monomethyl acetamide.

As to the dimensioning and operating conditions of the second column there is only mentioned that a classic column type and classic operating conditions had been used. In the examples there is indicated that the second column is operated at a pressure of 400 mm Hg and a top temperature of 143° C. and that the purified DMAc had a residual content of about 225 ppm acetic acid as well as of about 225 ppm water. Therefore, it does not meet the strict specification requirements, as defined in the present patent application for pure DMAc.

It is an object of the present invention, therefore, to provide a process for distillatively purifying crude DMAc which ensures the achievement of the required specifications, in particular for solutions spinning for producing elastic polyurethane block copolymer fibers as well as hollow fibers.

Crude DMAc contains as main components besides DMAc amines, acetic acid and water. The content of acetic acid in acid include DMAc to be purified by the process of the invention does not exceed 20 weight-%. As water-containing crude DMAc there is understood herein below a crude DMAc with a water content between 1 and 99 weight-% or also of between 2 to 99 weight-% and between 80 and 98 weight-% especially between 95 and 98 weight-%, or also between 1 and 6 weight-%.

Moreover, the process should ensure the separation of the water from crude DMAc in a degree of purity, especially with a residual content of DMAc of less than 50 ppm which allows its rinse or its unproblematic deposing in waste water. We have found that this object is achieved by a process for distillatively purifying crude dimethylacetamide (crude DMAc) comprising DMAc, low boilers and high boilers by removing the low boilers and the high boilers to obtain pure DMAc in one of the column configurations listed hereinbelow:

(I) a main column with sidestream column or (II) a dividing wall column, which comprises operating at least the main column in column configuration (I) and the dividing wall column in column configuration (II) at a top pressure in the range from 0.5 to 1.8 bar absolute.

It has been found that, surprisingly, working at atmospheric pressure or at a pressure slightly above or below atmospheric pressure provides a degree of purity of the DMAc obtained by distillation which is substantially better than in the case of existing processes which are operated under reduced pressure and therefore at substantially lower temperatures for reducing the formation of impurities due to decomposition or side reactions.

In contrast, the inventors have found that, surprisingly, it is precisely a pressure and therefore a temperature rise which are required for the achievement of a pure product having a lower proportion of impurities.

DMAc has a boiling point at atmospheric pressure of 166° C.

In the present context, low boilers refer to substances whose boiling point is below the boiling point of DMAc and high boilers to substances whose boiling point is above the boiling point DMAc.

In the present process, low boilers are in particular water, and in addition dimethylamine and diethylamine.

High boilers are in particular ethanolamines, and also heavy ends, i.e. high molecular weight decomposition products in the form of highly viscous liquids or solids.

A column in stripping mode refers to a column which has separating internals only below the feed of the mixture to be separated in the column. In contrast, a column in rectifying mode has separating internals only above the feed of the mixture to be separated in the column.

As is well known, a dividing wall column refers to a column having a dividing wall which is arranged in the longitudinal direction of the column and prevents mixing of liquid and vapor streams in regions of the column. The dividing wall divides the column interior in a known manner into a feed region, a withdrawal region, an upper combined column region and also a lower combined column region.

In the present separating task, low boilers and high boilers have to be removed from their starting mixture and the product of value, pure DMAc, has to be obtained as the medium boiler.

This separating task can be solved in particular by one of the following column configurations:

(I) a main column with a sidestream column or (II) a dividing wall column.

According to the invention, in each of the above-listed column configurations, at least the column in which the low boiler, water, has not yet been substantially removed has to be operated at a pressure in the range from 0.5 to 1.8 bar absolute, i.e. at atmospheric pressure or at slightly reduced or increased pressure compared to atmospheric pressure.

The top pressure in the abovementioned columns is preferably in the range from 0.8 to 1.5 bar absolute, more preferably in the range from 1.0 to 1.3 bar absolute.

It is also possible that the sidestream column in column configuration (I) is also operated at a top pressure in the range from 0.5 to 1.8 bar absolute, preferably from 0.8 to 1.5 bar absolute, more preferably from 1.0 to 1.3 bar absolute.

The crude DMAc stream can be fed either in gaseous or in liquid form, although feeding in the liquid state is advantageous for energy reasons.

In all column configurations, the separating internals used may in principle be any known internals, in particular trays, random packings or structured packings.

Suitable internals are customary internals such as commercial trays, random packings or structured packings, for example bubble-capped trays, tunnel-capped trays, valve trays, sieve trays, dual-flow trays and mesh trays, Pall rings, Berl saddles, wire mesh rings, Rasching rings®, Intalox® saddles, Interpak® random packings and Intos®, and also structured packings, for example Sulzer Mellapak®, Sulzer Optiflow®, Kuhni Rombopack® and Montz Pak® and also fabric packings. Preference is given to high-performance packings.

Preference is given to using separating internals having long delay times, in particular trays, below the feed of the crude DMAc stream to be purified, i.e. in the stripping section of the main column in column configuration (I) and in the stripping section of the dividing wall column in column configuration (II). The internals having longer residence times ensure increased dissociation of the acetic acid-diethylamine adduct.

The diameter of the columns is determined by the throughputs desired in each case and can be easily determined by those skilled in the art by the general rules of engineering.

The design of the columns with regard to height and positioning of inlets and outlets can be determined by the known concept of theoretical plates in combination with the selected internals.

As is known, a theoretical plate refers to that unit of the column which causes enrichment of the less volatile components in accordance with the thermodynamic equilibrium, provided that there is ideal mixing, liquid and gaseous phase are in equilibrium and there is no entrainment of liquid drops (cf. Vauck, Mullen: Grundoperationen chemischer Verfahrenstechnik, VCH-Verlagsgesenschaft mbH, Weinheim, 1988).

The number of theoretical plates for the region above the feed of the crude DMAc stream to be purified, i.e. for the upper region of the main column in column configuration (I) or for the region above the upper end of the dividing wall in the dividing wall column, is determined by customary process technology considerations depending on the low boiler content in the crude DMAc and the permissible loss of DMAc via the top of the first column.

The number of theoretical plates in the stripping section of the main column in column configuration (I) or of the dividing wall column below the dividing wall in column configuration (II) is preferably determined within the range from 5 to 30, in particular within the range from 10 to 25, more preferably within the range from 12 to 18.

The main column of column configuration (I) or the dividing wall column are preferably each equipped with a bottom evaporator and a condenser at the top of the column.

Advantageously, the temperature at the top of the main column or the dividing wall column is set within the range from 70 to 130° C., preferably within the range from 85 to 115° C., more preferably within the range from 95 to 105° C. and the temperatures in the bottom of the main column or of the dividing wall column are each set within the range from 150 to 200° C., preferably within the range from 160 to 190° C., more preferably within the range from 170 to 180° C.

The distillative purification of crude DMAc is advantageously carried out in a column configuration (I) whose main column has a gaseous sidestream and whose sidestream column is operated in rectifying mode. The sidestream column from column configuration (I) this differs from classic distillation columns, as they are used for example in the two-column process of the state of the art, inter alia because it is not equipped with a bottom reboiler and because it is dimensioned with less separating stages. Moreover, it can be dimensioned by the man skilled in the art in a few number of routine experiments or calculations on the basis and depending on the composition of the sidestream from the main column which is feed to the sidestream column. The sidestream column can be equipped with normal column internals, column packings being preferred.

The main column preferably has a smaller diameter above the gaseous sidestream takeoff compared to the region of the main column below the gaseous sidestream takeoff.

The distillative purification can further be carried out in a column configuration (I) in which the main column has a liquid sidestream and the sidestream column is operated in stripping mode.

The high boiler take-off of the mentioned column configurations (I) or (II) contains in addition to acetic acid also the product of value, DMAc, because DMAc and acetic acid form a high boiling azeotrope. Therefore, the complete thermal separation by distillation of acetic acid and DMAc is not possible.

The high boiling azeotrope of acetic acid and DMAc from the bottom of the main column or the dividing wall column is drawn off and can be used in a energetic advantageous way for recovering the DMAc contained there by neutralization with alkali and recoveraing the DMAc by evaporating the product obtained by neutralization in a falling film evaporator or viper blade evaporator, optionally at reduced pressure. The neutralization and the evaporation following neutralization can be done either continuously or discontinuously.

Advantageously, the distillative purification is operated continuously.

The process according to the invention thus provides, in a surprisingly simple manner, crude DMAc which fulfills the required specifications with regard to water content, pH and electrical conductivity, by distillation at atmospheric pressure or at slightly reduced or increased pressure compared to atmospheric pressure. Compared to a mode of operation under reduced pressure, as hitherto appeared to be necessary in the prior art for the purification of DMAc, the mode of operation at or virtually at atmospheric pressure is substantially more economically viable, especially with regard to capital and operating costs. In addition, the capacity of the apparatus rises with the increase in the operating pressure, since the gas flow rate at a constant gas composition falls as a consequence of the higher gas density.

The invention is illustrated by a drawing and an example which follow.

FIG. 1 shows a preferred example of the process according to the invention in which a column configuration (I) having a main column MC and a sidestream column SC is selected.

A crude DMAc stream 1 is fed to the middle region of the main column MC. A low boiler-containing stream 3 is removed at the top of the column and a high boiler-containing stream 4 from the bottom of the column. A gaseous stream is removed via a sidestream takeoff which still contains high-boiling impurities which impair the specification, in particular acetic acid, and is purified in the sidestream column SC which is operated in rectifying mode to obtain a pure DMAc stream 6 at the top of the column.

Figure 2:
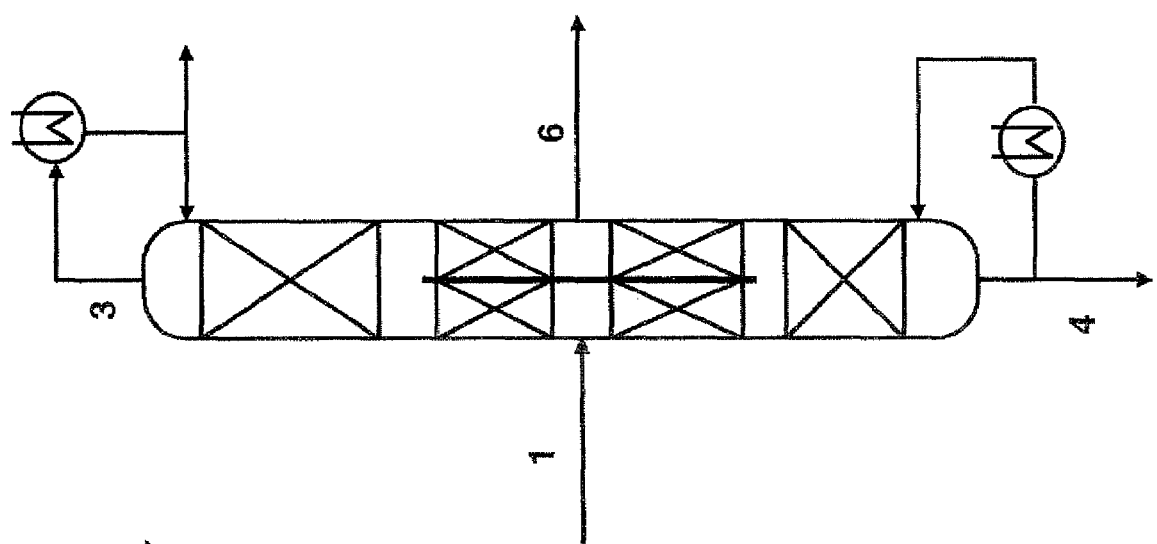

FIG. 2 shows an example of the process according to configuration (II) where stream 1 is fed to the main column. Stream 3 is removed at the top of the column and stream 4 from the bottom of the column. Stream 6 is also shown as being removed from the column.

EXAMPLE

In a column configuration (I) corresponding to the schematic diagram in FIG. 1, a liquid crude DMAc stream 1 having following components:

DMAc 99.2% by weight, dimethylamine 6 ppm, DMF 0.2% by weight, water 0.3% by weight, acetic acid 100 ppm, formic acid 350 ppm, phosphoric acid 50 ppm and heavy ends 0.2% by weight was fed at a temperature of 20° C. to the 30th theoretical plate of a main column having 57 theoretical plates, the plates being counted from bottom to top.

A gaseous sidestream was removed at a temperature of 171.9° C. from the 9th theoretical plate and had the following composition:

DMAc 99.9% by weight, DMF 720 ppm and acetic acid 280 ppm.

The specification-impairing concentration of acetic acid of 280 ppm could be reduced in the sidestream column to a non-specification-impairing 20 ppm in the top stream 6 which is removed as the pure DMAc stream. The main column MC and the side column SC were operated at atmospheric pressure.

We claim:

1. A process for distillatively purifying crude water-containing dimethylacetamide (crude DMAc) comprising DMAc, low boilers and high boilers removing the low boilers and the high boilers to obtain DMAc which is purer than crude DMAc, in one of the column configurations listed hereinbelow:
    (I) a main column (MC) with sidestream column (SC) or
    (II) a dividing wall column (DWC),
    which comprises operating at least the main column (MC) in column configuration (I) and the dividing wall column (DWC) in column configuration (II) at a top pressure in a range from 0.5 to 1.8 bar absolute.

2. A process as claimed in claim 1, including operating at least the main column (MC) in column configuration (I) and the dividing wall column (DWC) in column configuration (II) at a top pressure in a range from 0.8 to 1.5 bar absolute.

3. A process as claimed in claim 2, wherein operating at least the main column (MC) in column configuration (I) and the dividing wall column (DWC) in column configuration (II) at a top pressure in a range from at 1.0 to 1.3 bar absolute.

4. A process as claimed in claim 2, wherein operating the sidestream column (SC) in column configuration (I) at a top pressure in a range from 1.0 to 1.3 bar absolute.

5. A process as claimed in claim 1, wherein the sidestream column (SC) in column configuration (I) is operated at a top pressure in the range from 0.5 to 1.8 bar absolute.

6. A process as claimed in claim 5, wherein operating the sidestream column (SC) in column configuration (I) at a top pressure in a range from 0.8 to 1.5 bar absolute.

7. A process as claimed in claim 1, wherein separating internals having delay times, installing trays in the stripping section of the main column (MC) in column configuration (I) or in a stripping section of the dividing wall column (DWC) in column configuration (II).

8. A process as claimed in claim 7, wherein providing from 10 to 25 theoretical plates in the stripping section of the main column (MC) or of the dividing wall column (DWC).

9. A process as claimed in claim 7, wherein providing from 12 to 18 theoretical plates in the stripping section of the main column (MC) or of the dividing wall column (DWC).

10. A process as claimed in claim 1, wherein providing from 5 to 30 theoretical plates in a stripping section of the main column (MC) or of the dividing column (DWC).

11. A process as claimed in claim 1, wherein equipping the main column (MC) or the dividing wall column (DWC) each with a bottom evaporator and a condenser at the top of the column.

12. A process as claimed in claim 11, wherein setting the temperatures at the top of the main column (MC) or of the dividing wall column (DWC) within a range from 85 to 115° C. and setting the temperatures in the bottom of the main column (MC) and of the dividing wall column (DWC) each within a range from 160 to 190° C.

13. A process as claimed in claim 11, wherein setting the temperature at the top of the main column (MC) or of the dividing wall column (DWC) within a range from 95 to 105° C. and setting the temperatures in the bottom of the main column (MC) and the dividing wall column (DWC) each within a range of 170 to 180° C.

14. A process as claimed in claim 1, wherein setting the temperature at the top of the main column (MC) or of the dividing wall column (DWC) within a range from 70 to 130° C. and setting the temperatures in the bottom of the main column (MC) and of the dividing wall column (DWC) each within a range from 150 to 200° C.

15. A process as claimed in claim 1, wherein carrying out the distillative purification of crude DMAc in a column configuration (I) whose main column (MC) has a gaseous sidestream take off and whose sidestream column (SC) is operated in rectifying mode.

16. A process as claimed in claim 15, wherein having the main column (MC) with a smaller diameter above the gaseous sidestream takeoff compared to the region of the main column (MC) below the gaseous sidestream takeoff.

17. A process as claimed in claim 1, wherein carrying out the distillative purification in a column configuration (I) in which the main column (MC) has a liquid sidestream and the sidestream column (SC) is operated in stripping mode.

18. A process as claimed in claim 1, which is operated continuously.

* * * * *